United States Patent [19]

Hasson

[11] Patent Number: 4,872,456

[45] Date of Patent: Oct. 10, 1989

[54] TEMPLATE INCISION DEVICE

[76] Inventor: Harrith M. Hasson, P.O. Box 14898, Chicago, Ill. 60614

[21] Appl. No.: 119,488

[22] Filed: Nov. 12, 1987

[51] Int. Cl.⁴ ............................................. A61B 17/28
[52] U.S. Cl. .................................................... 128/321
[58] Field of Search ........... 128/346, 321, 322, 303 R, 128/318, 354, 314; 604/22, 174

[56] References Cited

U.S. PATENT DOCUMENTS

| | | | |
|---|---|---|---|
| 848,126 | 3/1907 | Roosevelt | 128/346 |
| 2,011,169 | 8/1935 | Wappler | 128/321 |
| 2,114,695 | 4/1938 | Anderson | 128/321 |
| 2,137,710 | 11/1938 | Anderson | 128/321 |
| 2,214,985 | 9/1940 | Bachmann | 128/321 |
| 2,234,686 | 3/1941 | Walter | 604/174 |
| 3,865,113 | 2/1975 | Sharon et al. | 128/303.1 |
| 3,895,636 | 7/1975 | Schmidt | 128/321 |
| 3,899,829 | 8/1975 | Storm et al. | 128/318 |
| 3,967,625 | 7/1976 | Yoon | 128/303.1 |
| 4,192,313 | 3/1980 | Ogami | 128/321 |
| 4,240,431 | 12/1980 | Komiya | 128/303.1 |
| 4,249,533 | 2/1981 | Komiya | 128/303.1 |
| 4,520,815 | 6/1985 | Marinoff | 128/303 R |
| 4,598,699 | 7/1986 | Garner et al. | 128/303 R |
| 4,726,368 | 2/1988 | Morris | 128/303 R |
| 4,760,840 | 8/1988 | Fournier, Jr. et al. | 128/303.1 |

*Primary Examiner*—John D. Yasko
*Attorney, Agent, or Firm*—Wood, Dalton, Phillips, Mason & Rowe

[57] ABSTRACT

A device for use in laser surgery has a first jaw and a second jaw pivotable to engage the first jaw to clamp tissue therebetween. The first and second jaws may be manually pivoted and secured together for clamping. The second jaw has a slot therethrough which is open to the first jaw to provide a guide for laser cutting. A third jaw is also provided for clamping tissue between it and the first jaw, said third jaw also having a slot therethrough and open to the first jaw. The jaws are pivoted to the distal end of a sleeve with a hollow interior. Control rods extend through the sleeve interior and connect to the respective jaws in an overcenter configuration. The control rods may, at the proximal end of the sleeve, be manually manipulated in order to pivot the jaws for manipulation at the surgical site.

21 Claims, 2 Drawing Sheets

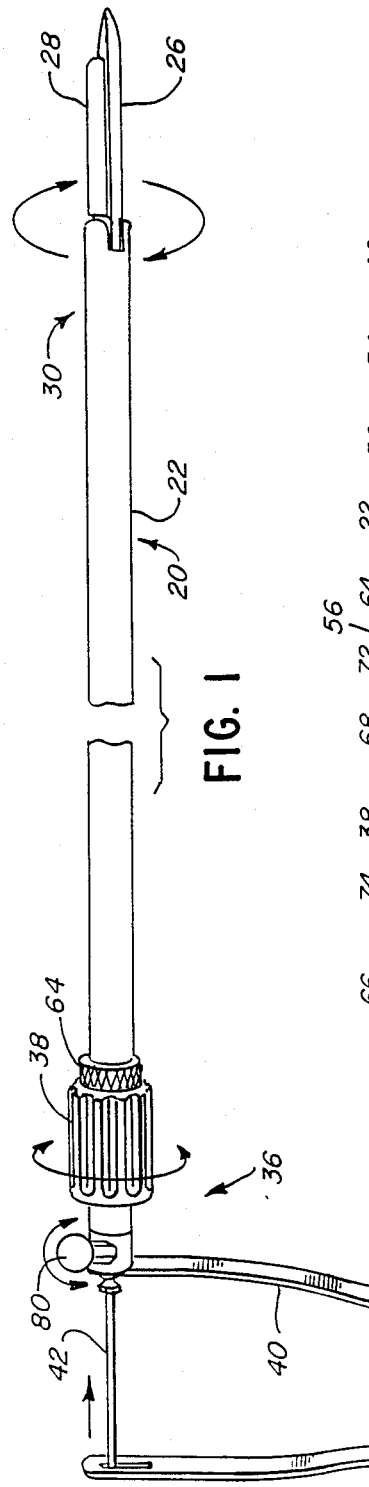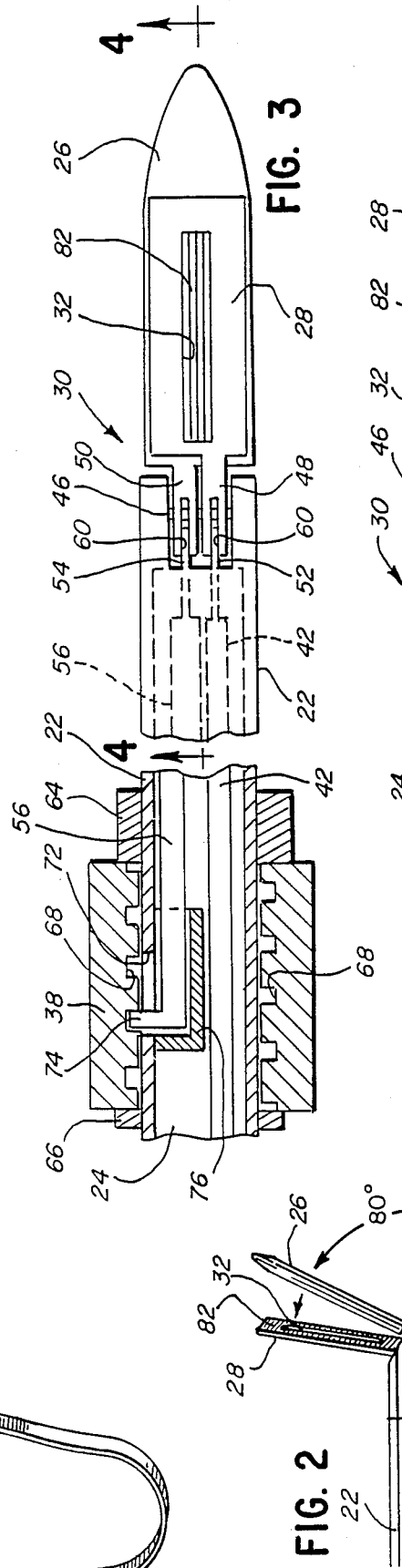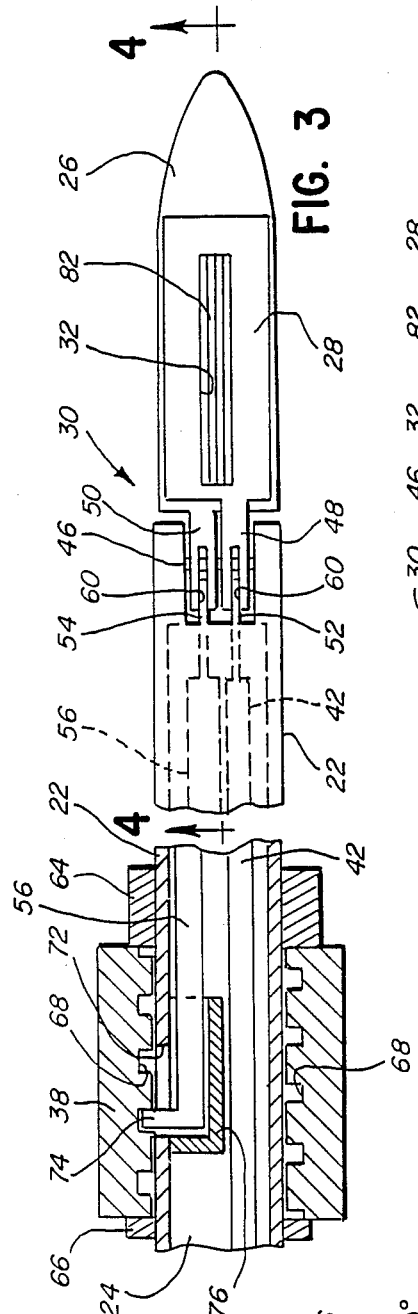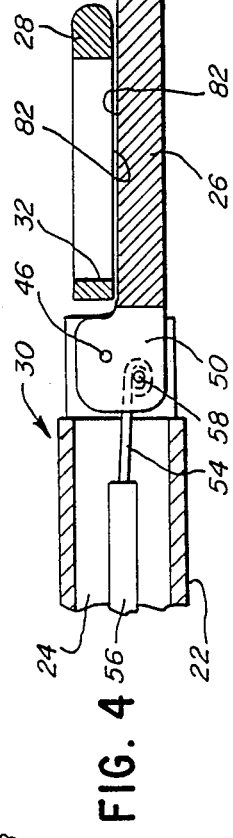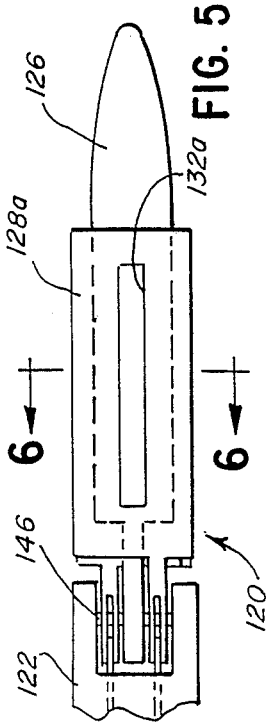

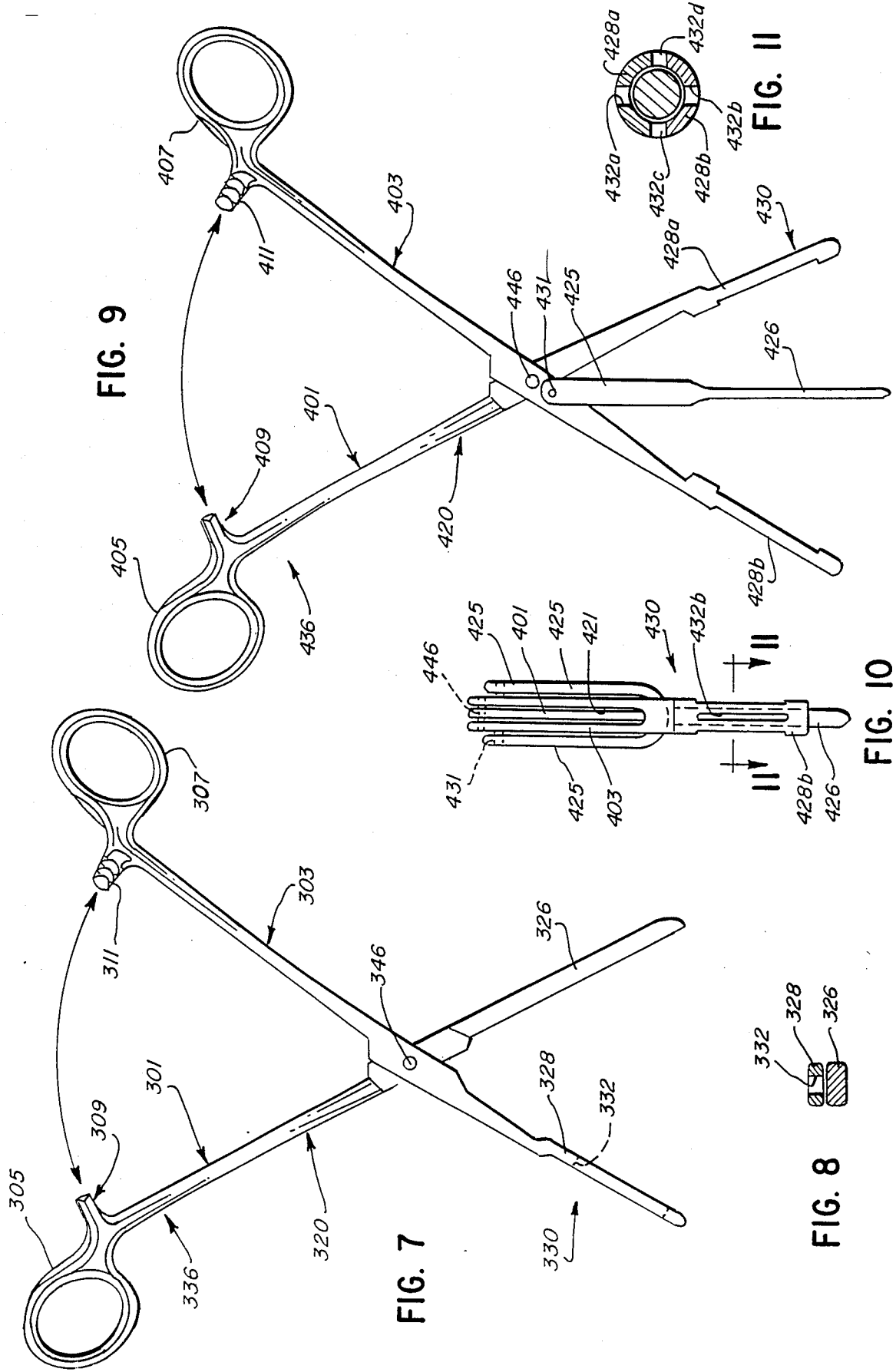

TEMPLATE INCISION DEVICE

TECHNICAL FIELD

The present invention relates to a surgical device.

BACKGROUND ART

Incisions for abdominal and pelvic surgery may be minimized by laparoscopic surgery in which, rather than a long incision, various smaller openings are provided by a plurality of "nails" into the abdominal area, with a sheath being provided around the "nail" to maintain the opening when the "nail" is withdrawn. Various other instruments may then be inserted through the opening in the sheath, such as lasers, forceps, and fiber-optic cameras for viewing the areas.

It is, however, difficult at times to obtain suitable access to some operative sites without providing an increased number of abdominal puncture sites. Gaining access by increasing the number of abdominal entry sites can produce intra-abdominal clashing of the instruments and increase operative difficulty.

Also, in laser surgery there is a danger that the laser will make not only the desired incision but also cut healthy tissue behind the incision. One method which has been used to prevent this where possible has been to provide a backing structure (which will not reflect the laser beam) beneath the tissue being cut and above the healthy tissue. Even with a backing structure, however, it can be difficult to provide a laser cut at right angles to the tissue (as is desirable), and it is also difficult to ensure that the incision is straight rather than jagged. Further, with multiple incisions (particularly when incisions are made in tubular body components, such as during salpingostomy procedures), it is often difficult to consistently provide the desired uniform spacing between incisions.

Still further, the blood vessels which are adjacent laser cuts are frequently not small enough to allow the laser to provide effective hemostatis, and therefore there is often undesirable bleeding at the incision.

The present invention is directed toward overcoming one or more of the problems as set forth above.

SUMMARY OF THE INVENTION

In one aspect of the present invention, a device for use in laser surgery is provided including a first jaw and a second jaw pivotable to engage the first jaw to clamp tissue therebetween. The first and second jaws may be manually pivoted and secured together for clamping. The second jaw has a slot therethrough which is open to the first jaw to provide a guide for laser cutting.

In another aspect of the present invention, a third jaw is provided for clamping tissue between it and the first jaw, said third jaw also having a slot therethrough and open to the first jaw.

In still another aspect of the present invention, a sleeve with a hollow interior is provided with the first and second jaws pivoted to its distal end. First and second control rods extend through the sleeve interior and connect to the first and second jaws respectively in an overcenter configuration. The control rods extend to the proximal end of the sleeve and may be manually manipulated in order to pivot the first and second jaws respectively for manipulation at the surgical site.

It is an object of the present invention to provide a device which ensures that surgical incisions by a laser are precisely straight and, in tubal incisions, are geometrically equidistant.

It is another object of the present invention to provide a device which prevents the laser beam from damaging healthy tissue behind and around the tissue which is cut.

Another object of the present invention is to ensure that the laser beam be directed at right angles to the surgical site to provide optimal laser vaporization.

Still another object of the present invention is to provide a device which will improve the hemostatis adjacent laser incisions.

Still another object of the present invention is to minimize the number of puncture sites for entry of surgical instruments which may be required in laparoscopic surgery.

Yet another object of the present invention is to provide a device which may be easily manipulated to grasp and/or cut tissue in various pelvic and abdominal planes during laparoscopic surgery.

BRIEF DESCRIPTION OF THE DRAWINGS

FIG. 1 is a perspective view of one embodiment of the template incision device;

FIG. 2 is a persepctive view showing the distal end of the device in a different position;

FIG. 3 is a partial cross-sectional top view of the FIG. 1 embodiment;

FIG. 4 is a cross-sectional view taken along line 4—4 of FIG. 3;

FIG. 5 is a top view of the distal end of a second embodiment of the present invention;

FIG. 6 is a cross-sectional view taken along line 6—6 of FIG. 5;

FIG. 7 is a plan view of a third embodiment of the present invention;

FIG. 8 is a cross-sectional view of the distal end of the FIG. 7 embodiment when closed;

FIG. 6a is a cross-sectional view of a modification of the distal end of the incision device in FIG. 1 to include scissor edges;

FIG. 9 is a plan view of yet another embodiment of the present invention;

FIG. 10 is a side view of the distal end of the FIG. 9 embodiment when closed; and FIG. 11 is a cross-sectional view taken along line 11—11 of FIG. 10.

DESCRIPTION OF THE PREFERRED EMBODIMENTS

A first embodiment of the incision device 20 of the present invention is shown in FIGS. 1-4. The device 20 includes a straight sleeve 22 having a hollow interior 24 (see FIGS. 3-4) with a base jaw 26 and a template jaw 28 pivotably secured at the distal end 30 thereof. The template jaw 28 includes a slot 32 therethrough. Both jaws 26,28 are provided with a rough texture so that they will not dangerously reflect laser beams during surgery.

At the proximal end 36 of the sleeve 22 is a knob 38 which may be manually turned to pivot the base jaw 26 up to about 80° (see FIG. 2) and a leaf spring 40 with a control rod 42 which may be manipulated to pivot the template jaw 28 (see FIG. 2) as will be apparent from the description hereafter.

Referring now to FIGS. 3-4, the device includes a pin 46 about which the jaw flanges 48,50 pivot. Rigid connectors 52,54 to the control rods 42,56 are suitably secured to the jaws 28,26 (e.g., by looping around pins 58 in a slot 60 in each jaw flange 48,50) in an overcenter configuration (see FIG. 4). It will be appreciated by those skilled in the art that axial movement of the control rods 42,56 to the right in FIG. 4 (i.e., out of the sleeve 22) will cause the associated jaws 28,26 to pivot up (such as shown in FIG. 2). Similarly, movement of the control rods 42,56 in the opposite direction will cause opposite pivoting of the jaws 28,26.

Pivoting of the base jaw 26 is controlled by the knob 38 which is rotatably disposed over the sleeve 22 and held against axial motion by two shoulders 64,66 fixed on the sleeve 22. The knob 38 includes a helical thread 68 around its inner face 70. The sleeve has an opening 72 therethrough, and a radial flange 74 on the end of the control rod 56 extends through that opening 72 and is received in the knob helical thread 68. The flange 74 is suitably held in engagement with the thread 68, for example, by a housing 76 fixed in the sleeve 22 as shown. Accordingly, the control rod 56 may be axially reciprocated by turning the knob 38, and the base jaw 26 may be maintained in a selected pivoted position. Still other structures for positively controlling the control rod 56 could also be used with the device.

The control rod 42 of the template jaw 28 is fixed to one of the leaf spring 40 (the other end of the leaf spring 40 being fixed to the sleeve 22) so that the rod 42 is biased rearwardly (i.e., to the left in FIGS. 1-4). As a result, the template jaw 28 is biased toward pivoting against the base jaw 26 except when the user manually overcomes the leaf spring force and pushes the control rod 42 to the right in FIGS. 1-4.

A screw 80 is also provided in the sleeve 22 which, when manually turned, may be caused to engage the control rod 42 within the sleeve 22 to frictionally secure the rod 42 and associated template jaw 28 in a particular position when desired.

The device 20 thus provides significant advantages when used during laparoscopic surgery. With the jaws 26,28 aligned with the sleeve 22 as shown in FIG. 1, the device 20 may be inserted into the opening in a sheath in the patient (as described in the Background Art section hereof). Then, by turning the knob 38 and squeezing the leaf spring 40, as well as by turning the sleeve 22 about its axis, the jaws 26,28 may be positioned to grasp tissue not merely along the axis of the sheath opening, but anywhere within a hemispherical space at the end of the sleeve 22. This therefore allows the surgeon to minimize the number of entry points which might be required through the patient's abdomen.

By positioning the base jaw 26 beneath a selected tissue and then releasing the leaf spring 40 to bias the template jaw 28 against the base jaw 26, the tissue may be clamped securely therebetween in order to move it as desired. Opposing serrations 82 (see FIGS. 2 and 3) may be provided in the facing surfaces of the jaws 26,28 in order to securely grasp the tissue and enable it to be moved as desired. (It should be understood that although the jaws are shown together in the FIG. 4 cross-section as well as cross-sections of other embodiments, the jaws may be configured when closed so as to be spaced apart a distance substantially equal to the thickness of the tissue which it is anticipated will be grasped.)

The above device 20 can also be used with electro-coagulation by adding electrical insulation and/or constructing components at the distal end 30 from teflon or a similar electrically non-conductive material.

Still further, this device 20 may be constructed with conventional sharp scissor blades, as shown at 26', 28' in FIG. 6a or alligator or biopsy forceps or the like, instead of the jaws 26, 28 shown, and the above advantages relating to area of reach and minimization of entry points may be obtained with those types of instruments as well.

The slot 32 in the template jaw 28 further functions as an extremely valuable guide for incisions. Particularly in laser surgery, it is difficult not only to make a straight incision, but also to insure that the incision is made at 90° to the tissue. It is also difficult to cut through only the tissue in which the incision is desired without damaging other tissue behind it. With the jaws 26,28 of the present invention, the laser beam may be swept along the template jaw slot 32, and the tissue is thus held securely relative to the line of the incision and the laser is guided along that straight line to prevent jagged incisions. Further, the jaws 26,28 may be turned to orient the tissue and laser beam 90° relative to one another to provide the best exposure for optimal laser vaporization. Still further, the jaws 26,28 effectively compress the tissue adjacent the incision so as to compress the blood vessels therein to a reduced diameter, thereby increasing the effectiveness of laser hemostasis to reduce bleeding.

The distal end of a two template embodiment of the present invention is shown in FIGS. 5-6. This embodiment is particularly useful for facilitating salpingostomy procedures, as will be apparent. With this embodiment (in which components similar to those in the FIGS. 1-4 embodiment are given the same reference numerals plus 100), a cylindrical base jaw or probe 126 is provided pivotably secured to the pin 146 on the end of the shaft 122. Also pivotably secured to the shaft about the pin 146 are a pair of semi-cylindrical template jaws 128a,128b which are adapted to close substantially around the cylindrical base jaw 126 as shown in FIG. 6. Each of these template jaws 128a,128b include slots 132a,132b and additionally include half-slots along their edges which define yet another set of slots 132c,132d at their point of engagement when closed.

A knob and leaf spring such as shown in the FIG. 1 embodiment may be provided to position the two template jaws 128a,128b and the base jaw 126 (which pivots freely between the template jaws 128a,128b). Thus, by pivoting one template jaw 128a by a knob structure such as shown in the FIG. 1-4 embodiment, the base jaw 126 and other template jaw 128b may be oriented at an angle relative to the axis of the shaft 122 in order to cover a semi-spherical area such as discussed with respect to the first embodiment.

Alternatively, either one or separate leaf springs could be provided with both template jaws 128a,128b so as to cause them to both bias shut against the base jaw 126 when manual pressure is released. Further, the base jaw 126 may be secured to a control rod manipulated by a knob such as shown in the FIG. 1 embodiment, with the template jaws 128a,128b both controlled by a single leaf spring biasing the template jaws 128a,128b against the base jaw 126 in whichever position it is oriented by the knob.

This device 120 is particularly useful in surgery commonly performed on fallopian tubes where it is necessary to provide uniformly spaced and uniformly long incisions around the tube. By locating the base jaw 126 within the tube and then closing the template jaws 128a,128b therearound, four slots 132a-d are provided which will allow the surgeon to make spaced incisions around the tube, with the ends of the slots 132a–d also ensuring that the length of the incisions will be uniform. In addition, the various other advantages of using the template device as previously discussed (i.e., minimizing entry points through the patient's abdomen, providing straight, non-jagged incisions, preventing damage to tissue behind the tissue being cut, allowing the tissue to be easily oriented at 90° relative to the laser, and improved hemostasis) are also provided in such surgery.

Yet another embodiment of the present invention is shown in FIGS. 7 and 8. The device 320, which is useable during open surgery where access is not as restricted as in laparoscopic procedures, includes a pair of handles 301,303 pivotable about a pin 346 (in FIGS. 7 and 8, components similar to those in the FIG. 1–4 embodiment are given the same reference numerals plus 300, and non-comparable components are identified by odd numbers).

A finger or thumb grip 305,307 is provided at the proximal end 336 of each handle 301,303. An interlocking detent surface 309,311 of a type which is known in the art may be provided on each handle 301,303, which surfaces 309,311 mate when the device 320 is closed to lock the handles 301,303 together. Transverse manual manipulation of the handles 301,303 will separate the mated surfaces 309,311 for unlocking.

A base jaw 326 and a template jaw 328 are provided on the distal end 330 of the handles 301,303. The template jaw 328 has a slot 332 therethrough.

The present invention may thus be used during open surgery to obtain many of the advantages described with respect to the FIG. 1–4 embodiment. Thus, a laser beam may be swept along the template jaw slot 332 to insure that a straight, non-jagged incision is made with the tissue cut at 90° relative to the laser beam. Further, the tissue is compressed by the jaws 326,328 in order to increase the effectiveness of laser hemostatis, thereby reducing bleeding.

Still another embodiment of the present invention is shown in FIGS. 9–11. This device 420, which is also useable during open surgery where access is less restricted, includes a pair of handles 401,403 pivotable about a pin 446 (in FIGS. 9–11, components comparable to those in the FIG. 5–6 and FIG. 7–8 embodiments are identified by reference numerals having the same last two digits, but preceded by a 4). One handle 403 includes a slot 421 therein within which the other handle 401 may freely move during pivoting, as best seen in FIG. 10.

Finger or thumb grips 405,407 are also provided at the proximal end 446 of each handle 401,403, and interlocking detent surfaces 409,411 are provided on each handle 401,403 which mate to lock the device 420 closed when desired.

A base jaw 426 is provided on the end of a U-shaped yoke 425 which is pivotably mounted around pins 431 on one of the handles 403.

Each handle 401,403 at its distal end 430 includes a template jaw 428a,428b. The template jaws 428a,428b are semi-cylindrical and adapted to mate around the cylindrical base jaw 426 in a manner similar to the FIG. 5–6 embodiment. Slots 432a,432b are centrally located on each of the template jaws 428a,428b, and half-slots are also provided along their edges so as to define another set of slots 432c,432d at their point of engagement when closed (see FIG. 11).

The distal end of the base jaw 426 is tapered and extends beyond the ends of the template jaws 428a,428b so as to allow the base jaw 426 to be securely held by the template jaws 428a,428b to function as a probe and to enable the base jaw 426 to be positioned where desired.

As with the FIG. 5–6 embodiment, this device 420 is particularly useful in surgery where it is necessary to provide uniformly spaced and uniformly long incisions around a tube.

Still other aspects, objects and advantages of the present invention may be obtained from a study of the drawings, the specification and the appended claims.

I claim:

1. A device for use in laser surgery, comprising:
   a first jaw having serrations on one surface;
   a second jaw pivotable to engage a facing surface with the first jaw one surface, said second jaw facing surface having opposite serrations for clamping tissue between said jaws, and said second jaw having a slot therethrough open to said first jaw to provide a guide for laser cutting; and
   means for pivoting said first and second jaws together for clamping,
   said first jaw having a solid surface to block passage of a laser beam directed through said slot in the second jaw with the first and second jaws together for clamping to thereby prevent damage to tissue behind said first jaw.

2. The device of claim 1, further comprising:
   a third jaw pivotable to engage said first jaw opposite said second jaw, said third jaw having a slot therethrough and open to said first jaw; and
   means for pivoting said first and third jaws together for clamping.

3. The device of claim 2, wherein said first jaw is cylindrical and said second and third jaws curved to match the first jaw, said second and third jaws further being spaced on either side when engaging said first jaw to define longitudinal openings therebetween to provide additional guides for laser cutting.

4. The device of claim 1, wherein a straight sleeve having a hollow interior and a proximal and distal end is provided and said first and second jaws are pivoted to the distal end of the straight sleeve, and further comprising:
   a first control rod extending through the sleeve interior and connected to said first jaw in an overcenter configuration;
   first means on said sleeve proximal end for axially moving said first control rod to pivot said first jaw;
   a second control rod extending through the sleeve interior and connected to said second jaw in an overcenter configuration; and
   second means on said sleeve proximal end for axially moving said second control rod to pivot said second jaw.

5. A device for use in laser surgery, comprising:
   a first jaw having serrations on one surface;
   a second jaw pivotable to engage a facing surface with the first jaw one surface, said second jaw facing surface having opposite serrations for clamping tissue between said jaws, and said second jaw having a slot therethrough open to said first jaw to provide a guide for laser cutting;
   means for pivoting said first and second jaws together for clamping;

wherein a straight sleeve having a hollow interior and a proximal and distal end is provided and said first and second jaws are pivoted to the distal end of the straight sleeve, and further comprising:
a first control rod extending through the sleeve interior and connected to said first jaw in an overcenter configuration;
first means on said sleeve proximal end for axially moving said first control rod to pivot said first jaw;
a second control rod extending through the sleeve interior and connected to said second jaw in an overcenter configuration; and
second means on said sleeve proximal end for axially moving said second control rod to pivot said second jaw,
wherein said second moving means comprises a handle with a leaf spring acting between the sleeve and second control rod to bias said second control rod toward pivoting said second jaw against said first jaw.

6. The device of claim 5, further comprising means on the sleeve for selectively fixing said second control rod against axial movement.

7. A device for use in laser surgery, comprising:
a first jaw having serrations on one surface;
a second jaw pivotable to engage a facing surface with the first jaw one surface, said second jaw facing surface having opposite serrations for clamping tissue between said jaws, and said second jaw having a slot therethrough open to said first jaw to provide a guide for laser cutting;
means for pivoting said first and second jaws together for clamping;
wherein a straight sleeve having a hollow interior and a proximal and distal end is provided and said first and second jaws are pivoted to the distal end of the straight sleeve, and further comprising:
a first control rod extending through the sleeve interior and connected to said first jaw in an overcenter configuration;
first means on said sleeve proximal end for axially moving said first control rod to pivot said first jaw;
a second control rod extending through the sleeve interior and connected to said second jaw in an overcenter configuration; and
second means on said sleeve proximal end for axially moving said second control rod to pivot said second jaw,
wherein said first moving means comprises:
a rotatable threaded nut fixed axially with respect to said sleeve; and
a follower on said first control rod received in said nut thread for shifting the first control rod axially as the threaded nut is rotated relative to the sleeve.

8. The device of claim 7, further comprising a knurled handled around said nut for manual turning of said nut.

9. A device for use in laparoscopic surgery, comprising:
a straight sleeve with a hollow interior and proximal and distal ends;
a first jaw;
means for pivotably mounting the first jaw to the distal end of the sleeve;
a second jaw;
means for pivotably mounting the second jaw to the distal end of the sleeve so that the second jaw is selectively engageable with the first jaw;
a first control rod extending through the sleeve interior and connected to said first jaw in an overcenter configuration;
first means on said sleeve proximal end for axially moving said first control rod to pivot said first jaw;
a second control rod extending through the sleeve interior and connected to said second jaw in an overcenter configuration; and
second means on said sleeve proximal end for axially moving said second control rod to pivot said second jaw.

10. A device for use in laparoscopic surgery, comprising:
a straight sleeve with a hollow interior and proximal and distal ends;
a first jaw pivotably mounted to the distal end of the sleeve;
a second jaw pivotably mounted to the distal end of the sleeve and engageable with the first jaw;
a first control rod extending through the sleeve interior and connected to said first jaw in an overcenter configuration;
first means on said sleeve proximal end for axially moving said first control rod to pivot said first jaw;
a second control rod extending through the sleeve interior and connected to said second jaw in an overcenter configuration; and
second means on said sleeve proximal end for axially moving said second control rod to pivot said second jaw,
wherein said first and second jaws include associated sharp edges to function as scissors.

11. The device of claim 9, wherein said first and second jaws have facing surfaces with opposite serrations for clamping tissue between said jaws.

12. A device for use in laparoscopic surgery, comprising:
a straight sleeve with a hollow interior and proximal and distal ends;
a first jaw pivotably mounted to the distal end of the sleeve;
a second jaw pivotably mounted to the distal end of the sleeve and engageable with the first jaw;
a first control rod extending through the sleeve interior and connected to said first jaw in an overcenter configuration;
first means on said sleeve proximal end for axially moving said first control rod to pivot said first jaw;
a second control rod extending through the sleeve interior and connected to said second jaw in an overcenter configuration; and
second means on said sleeve proximal end for axially moving said second control rod to pivot said second jaw,
wherein said second moving means comprises a handle with a leaf spring acting between the sleeve and second control rod for biasing said second control rod toward pivoting said second jaw against said first jaw.

13. The device of claim 12, further comprising means on the sleeve for selectively fixing said second control rod against axial movement.

14. A device for use in laparoscopic surgery, comprising:
a straight sleeve with a hollow interior and proximal and distal ends;
a first jaw pivotably mounted to the distal end of the sleeve;

a second jaw pivotably mounted to the distal end of the sleeve and engageable with the first jaw;

a first control rod extending through the sleeve interior and connected to said first jaw in an overcenter configuration;

first means on said sleeve proximal end for axially moving said first control rod to pivot said first jaw;

a second control rod extending through the sleeve interior and connected to said second jaw in an overcenter configuration; and second means on said sleeve proximal end for axially moving said second control rod to pivot said second jaw, wherein said first and second jaws have facing surfaces with opposite serrations for clamping tissue between said jaws, wherein said first moving means comprises:

a rotatable threaded nut fixedly axially with respect to said sleeve; and a follower on said first control rod received in said nut thread for shifting the first control rod axially as the threaded nut is rotated relative to the sleeve.

15. The device of claim 14, further comprising a knurled handle around said nut for manual turning of said nut.

16. The device of claim 9, wherein said second jaw includes a slot therethrough open to said first jaw.

17. The device of claim 9, further comprising:

a third jaw pivotably mounted to the distal end of the sleeve and engageable with the first jaw opposite the second jaw;

a third control rod extending through the sleeve interior and connected to said third jaw in an overcenter configuration; and third means on said sleeve proximal end for axially moving said third control rod to pivot said third jaw.

18. The device of claim 17, wherein said second and third jaws each include a slot therethrough open to said first jaw.

19. The device of claim 18, wherein said first jaw is cylindrical and said second and third jaws are curved to match the first jaw, said second and third jaws further being spaced on either side when engaging said first jaw to define longitudinal openings therebetween.

20. The device of claim 9, wherein said first and second jaws have facing surfaces with teeth for clamping tissue between said jaws.

21. A device for use in laser surgery, said device comprising:

a first jaw having a first clamping surface;

a second jaw having a second clamping surface; and means for moving the first and second jaws selectively (a) together for clamping tissue between said first and second clamping surfaces and (b) away from each other, said second jaw having a slot therethrough open to said first jaw to provide a guide for laser cutting, said first jaw having a solid surface to block passage of a laser beam directed through said slot in the second jaw with the first and second jaws together for clamping to thereby prevent damage to tissue behind said first jaw.

* * * * *